(12) United States Patent
Oklejas, Jr.

(10) Patent No.: US 11,002,181 B2
(45) Date of Patent: May 11, 2021

(54) METHOD AND SYSTEM FOR DETERMINING A CHARACTERISTIC OF A ROTATING MACHINE

(71) Applicant: FLUID EQUIPMENT DEVELOPMENT COMPANY, LLC, Monroe, MI (US)

(72) Inventor: Eli Oklejas, Jr., Newport, MI (US)

(73) Assignee: FLUID EQUIPMENT DEVELOPMENT COMPANY, LLC, Monroe, MI (US)

(*) Notice: Subject to any disclaimer, the term of this patent is extended or adjusted under 35 U.S.C. 154(b) by 0 days.

(21) Appl. No.: 16/857,468

(22) Filed: Apr. 24, 2020

(65) Prior Publication Data

US 2020/0347776 A1 Nov. 5, 2020

Related U.S. Application Data

(60) Provisional application No. 62/842,595, filed on May 3, 2019.

(51) Int. Cl.
*F02B 37/16* (2006.01)
*G01K 13/08* (2006.01)
(Continued)

(52) U.S. Cl.
CPC .............. *F02B 37/16* (2013.01); *F01D 17/02* (2013.01); *F01D 17/085* (2013.01); *F01D 21/12* (2013.01); *F02C 6/12* (2013.01); *G01K 13/08* (2013.01); *G01N 33/2835* (2013.01); *F05D 2220/40* (2013.01); *F05D 2270/303* (2013.01)

(58) Field of Classification Search
CPC .......... F02B 39/14; F02B 37/10; F02B 39/00; F02B 39/10; F02B 39/005; F02B 39/16; F01D 25/12; F01D 25/18; F01D 25/186; F01D 25/20; F01D 17/02; F01D 25/125; G01K 13/08; G01N 33/2835
See application file for complete search history.

(56) References Cited

U.S. PATENT DOCUMENTS 4,884,406 A * 12/1989 Kawamura ............. F02B 39/10
60/605.3
6,439,836 B1 * 8/2002 Pozivil .................. F01D 15/005
415/110
(Continued)

FOREIGN PATENT DOCUMENTS

EP          0102334 A1   3/1984
WO    WO-2018-217913 A1  11/2018

OTHER PUBLICATIONS

International Search Report and Written Opinion dated Sep. 18, 2020 in corresponding PCT Application No. PCT/US2020/030908 (12 pages).

*Primary Examiner* — Dominick L Plakkoottam
(74) *Attorney, Agent, or Firm* — Harness, Dickey & Pierce, P.L.C.

(57) ABSTRACT

A rotating machine has a stationary portion, and a rotating portion. The stationary portion and the rotating portion having a fluid passage therebetween. The stationary portion comprising a first fluid channel, a well, and a second fluid channel spaced apart from the first fluid channel. The first fluid channel fluidically is coupled to receive fluid from the fluid passage. A sensor is coupled to the stationary portion and is disposed at the well.

20 Claims, 3 Drawing Sheets

(51) Int. Cl.
*G01N 33/28* (2006.01)
*F01D 17/02* (2006.01)
*F01D 17/08* (2006.01)
*F02C 6/12* (2006.01)
*F01D 21/12* (2006.01)

(56) References Cited

U.S. PATENT DOCUMENTS

| | | | |
|---|---|---|---|
| 6,871,499 B1 * | 3/2005 | Allen | F02B 39/14 |
| | | | 60/608 |
| 8,016,545 B2 * | 9/2011 | Oklejas, Jr. | F04D 29/0416 |
| | | | 415/106 |
| 10,526,960 B2 * | 1/2020 | Kojima | F02B 39/00 |
| 10,598,092 B2 * | 3/2020 | Lee | F01M 11/02 |
| 2007/0034265 A1 * | 2/2007 | Mohr | F16L 27/0828 |
| | | | 137/580 |
| 2007/0292283 A1 | 12/2007 | Oklejas | |
| 2012/0088850 A1 * | 4/2012 | Rabovitser | C01B 3/386 |
| | | | 518/702 |
| 2014/0112762 A1 * | 4/2014 | Isogai | F04D 29/441 |
| | | | 415/121.3 |
| 2016/0202168 A1 * | 7/2016 | Knobloch | G01C 21/20 |
| | | | 701/3 |
| 2016/0254768 A1 * | 9/2016 | Falkowski | F02D 29/06 |
| | | | 290/40 C |
| 2018/0363501 A1 * | 12/2018 | Noda | F16C 27/045 |
| 2020/0056505 A1 * | 2/2020 | Sakamoto | F01D 25/243 |

\* cited by examiner

METHOD AND SYSTEM FOR DETERMINING A CHARACTERISTIC OF A ROTATING MACHINE

RELATED APPLICATION

This application is a non-provisional application of provisional application 62/842,595 filed May 3, 2019. The disclosures of which are incorporated by reference herein.

TECHNICAL FIELD

The present disclosure relates generally to a rotating machine, and, more specifically, to methods and systems for determining a characteristic such a temperature or particulates within the rotating machine.

BACKGROUND

The statements in this section merely provide background information related to the present disclosure and may not constitute prior art.

Referring now to FIG. 1, a rotating machine 10 has a housing 12 that has a pump portion 14 and a turbine portion 16. The pump portion 14 has a pump inlet 18 and a pump outlet 20. Pumpage passes from the pump inlet 18 and passes through a pump impeller 22 and exits the housing 12 through the pump outlet 20.

Turbine flow enters the turbine through a nozzle 23 and passes through a turbine impeller 24 and exits the turbine portion 16 through a turbine outlet 26. The pump impeller 22 and the turbine impeller 24 are coupled together with a rotor shaft 28. The rotor shaft 28 is supported within the housing 12 with a journal bearing 30. The housing 12 and the journal bearing 30 are stationary portions of the rotating machine 10. The pump impeller 22, the turbine impeller 24 and the rotor shaft 28 form the rotating portion of the rotating machine 10. A fluid passage or bearing clearance 32 allows a small amount of fluid to pass from the pump portion 14 to the turbine portion 16. The arrows 34 indicate the passage of fluid from the relatively high pressure of the pump portion 14 to the turbine portion 16. Forces in the direction toward the turbine portion 16 are absorbed at a thrust bearing 40.

As will be appreciated by those skilled in the art, the journal bearing 30 and the thrust bearing 40 rely on a thin film of fluid between the stationary surfaces and the moving or rotating surfaces. When the rotating surfaces contact the stationary surfaces during operation, the initial result will be heat generation followed by mechanical damage such as galling, chipping or complete failure. One way to detect the failure of a rotating machine is to provide vibration sensors to detect an increase in vibration. Vibration sensors, however, do not provide an immediate indication of fluid film failure. Also, vibration sensors tend to provide false/positives due to air ingestion, changes in operating conditions and the like. However, air ingestion or changes in operating conditions may be acceptable. Another way to provide failure detection is to provide a temperature sensor 42. The temperature sensor 42 is typically disposed in the housing 12 close to the thrust bearing 40. A significant delay is typical when the increase in bearing temperature is generated due to a failure. The delay may amount to over 1 minute of time. Such delays may allow a significant amount of damage to occur prior to disabling a system. Also, the monitoring of a journal bearing is not feasible because the temperature probe cannot be brought close enough to the bearing clearance to provide timely measurements.

SUMMARY

The present disclosure provides a system for providing quick and accurate temperature determinations due to a failure of a rotating machine. The present system and method provide a way to monitor failures in journal bearings and thrust bearings.

In one aspect of the disclosure, a rotating machine has a stationary portion, and a rotating portion. The stationary portion and the rotating portion having a fluid passage therebetween. The stationary portion comprising a first fluid channel, a well, and a second fluid channel spaced apart from the first fluid channel. The first fluid channel fluidically is coupled to receive fluid from the fluid passage. A sensor is coupled to the stationary portion and is disposed at the well.

In yet another aspect of the disclosure, a method of determining a temperature for a rotating machine comprises the steps of communicating a fluid through a fluid passage between a rotating portion and a stationary portion of the rotating machine, communicating the fluid from the fluid passage to a well through a first fluid channel, communicating fluid from the well to the fluid passage through a second fluid passage; and generating a sensor signal at a sensor operably coupled to the well.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
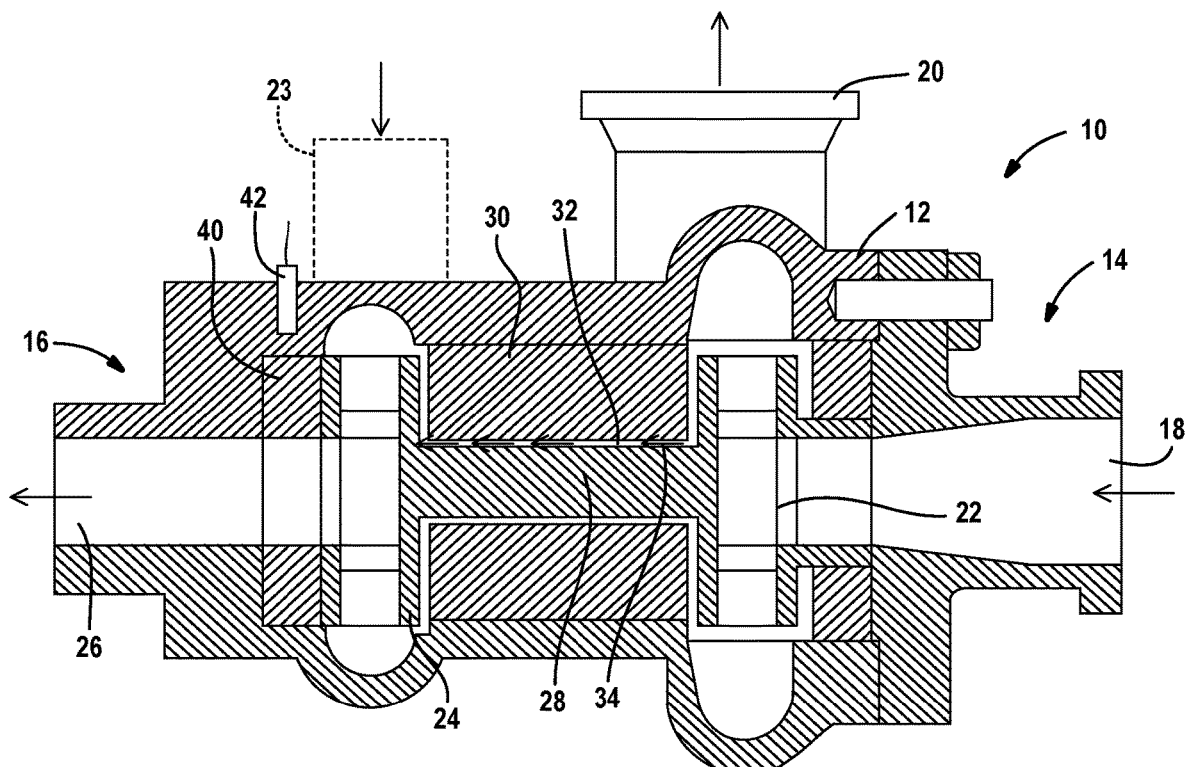
FIG. 1 is a cross-sectional view of a rotating machine according to the prior art.

The following description is merely exemplary in nature and is not intended to limit the present disclosure, application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

In the examples below, turbochargers are used as energy recovery devices that use energy in a turbine portion to pressurize fluid at a pump portion. Thus, the energy from the fluid in the turbine stream is recovered.

Figure 2:
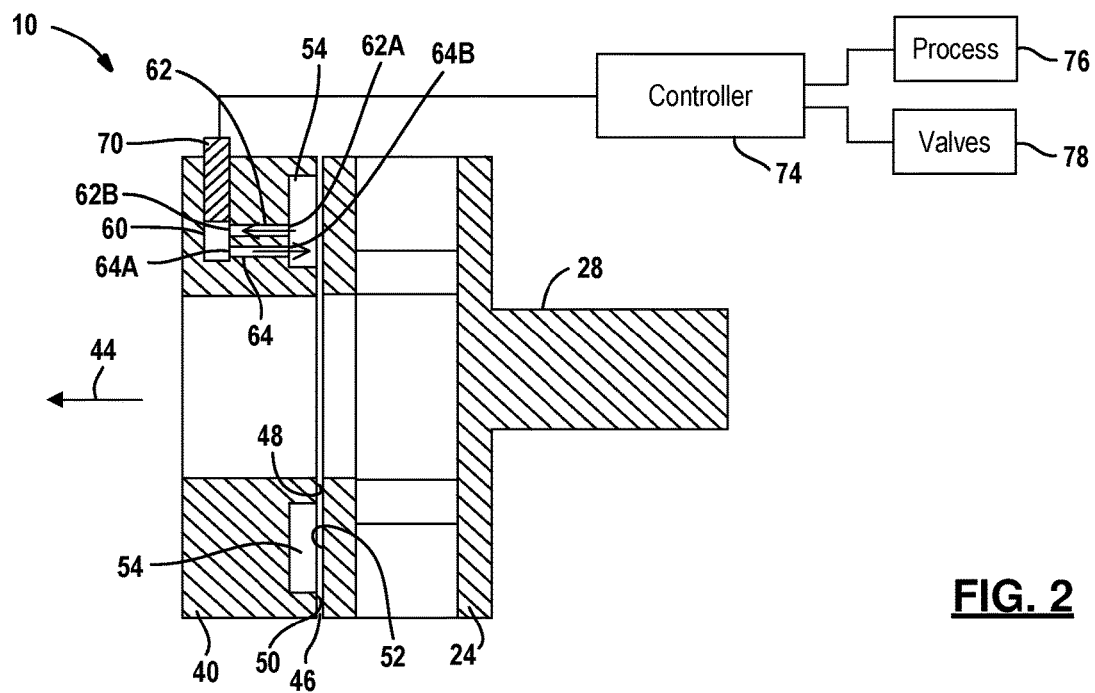
FIG. 2 is a cross-section view of a turbine impeller and shaft according to the present disclosure.

Referring now to FIG. 2, a partial rotor shaft 28 coupled to the turbine impeller 24 for an improved rotating machine 10' is set forth. Axial thrust in the direction of the axis of the rotor shaft 28 indicated by arrow 44 is resisted by lubricating fluid in a gap 46 between the thrust bearing 40 and the shroud of the turbine impeller 24. In particular, the thrust bearing 40 has an inner land 48 and an outer land 50 that is adjacent to the shroud surface 52 and have the gap 46 therebetween. That is, the inner land 48 and the outer land 50 are coplanar and parallel to the shroud surface 52. A pocket 54 extends axially into the thrust bearing 40. That is, the pocket 54 extends in a direction away from the shroud surface 52. The pocket 54 holds fluid that provides lubrication to the gap 46 between the shroud surface 52 and the inner land 48 and the outer land 50. During operation, a differential pressure gradient is formed within the pocket 54. The pocket 54 has a higher pressure radially outwardly and a lower pressure radially inwardly. That is, a static pressure gradient increases between the inner land 48 and the outer land 50 within the pocket 54.

A well 60 is disposed within the thrust bearing 40. The well 60 is fluidically coupled to the pocket 54 through a first fluid channel 62 and a second fluid channel 64. The arrows within the first fluid channel 62 and the second fluid channel indicate the direction of fluid flow. Because a greater pressure is developed at the pocket 54 near the first fluid channel 62, fluid flows from the pocket 54 to the well 60 through the first fluid channel 62. Fluid flows from 60 to the pocket 54 through the second fluid channel 64. The first fluid channel 62 has a first inlet 62A at the pocket 54 and a first outlet 62B. The second fluid channel 64 has a first inlet 64A and a first outlet 64B. Fluid from the pocket 54 moves from the inlet 62A to the outlet 62B of the first fluid channel 62. The fluid at the first outlet 62B of the first fluid 62 enters the thermal well 60. The higher pressure of the fluid forces the fluid toward the first inlet 64A of the second fluid channel 64 and through the first fluid channel 64 toward the first outlet 64B of the second fluid channel 64.

A sensor 70 is disposed within the well 60. The sensor 70 receives a continuous flow of fluid from the pocket 54 generated by the rotation of the turbine impeller 24. By way of example, the sensor 70 may be a temperature sensor or a particulate sensor. Any temperature increase or particles caused by a breakdown of the fluid between the inner land 48 and the outer land 50 relative to the turbine impeller 24 is detected rapidly. In one constructed embodiment, less than 1 second was required for detecting an increase in temperature at the sensor 70. The sensor 70 may be located a distance from the pocket 54 because the fluid flow is very rapid and may exceed 2-3 feet per second.

A controller 74 is coupled to the sensor 70. The controller 74 may be microprocessor based. The controller 74 is used for controlling various aspects of a process 76 or valves 78 in response to the sensor 70. That is, the controller 74 receives the sensor signal from the sensor 70 and may change the operation of the process 76 or the valves 78. In particular, valves 78 may be closed to stop the operation of the rotating machine such as the turbocharger 10. Of course, the controller 74 may change various conditions of operation to rapidly shutdown the turbocharger to prevent damage thereto. This will prolong the life of the turbocharger.

The process 76 may include controlling the power to a motor or other electrical components. The valves may be electrically controlled valves that may be turned off in response to the temperature signal from the temperature sensor 70.

Figure 3:
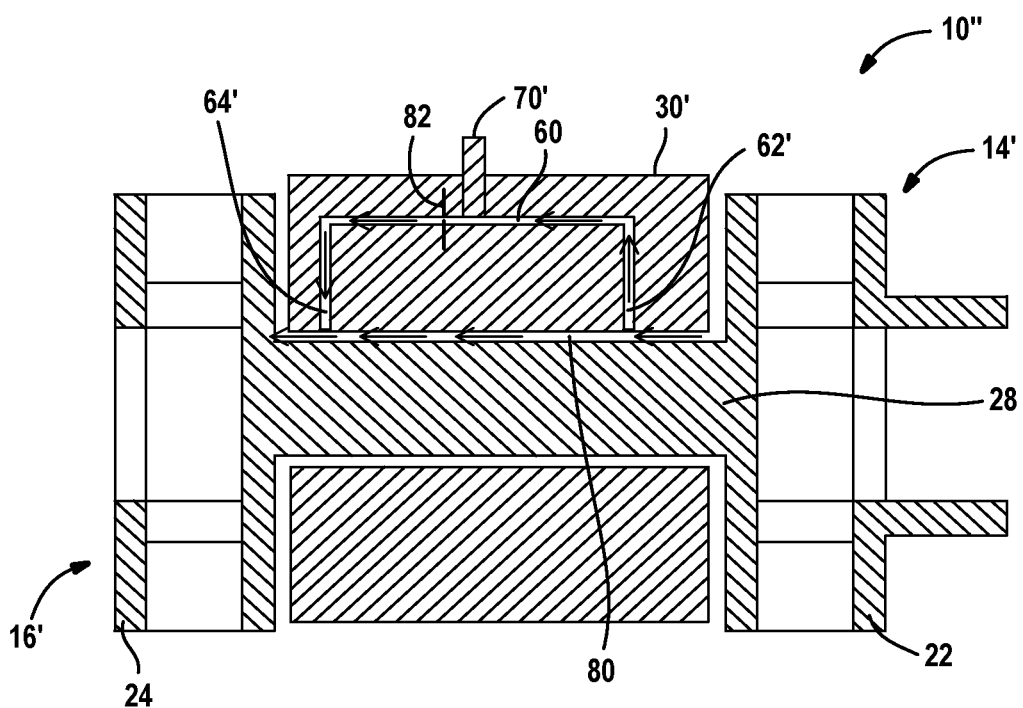
FIG. 3 is a second embodiment of a rotor shaft adjacent to a journal bearing.

Referring now to FIG. 3, the pump impeller 22, the turbine impeller 24 and the rotor shaft 28 are illustrated relative to a modified journal bearing 30' of a rotating machine 10". The journal bearing 30' has a first fluid channel 62' and a second fluid channel 64'. A fluid passage 80 is disposed between the rotor shaft 28 and the modified journal bearing 30'. The fluid adjacent to the pump impeller 22 is higher than the fluid pressure adjacent the turbine impeller 24. Thus, fluid flows through the fluid passage 80 from the pump portion 14 of the rotating machine 10' to the turbine portion 16'. The outer housing 12 of the rotating machine is not shown for simplicity. A well 60' connects the first fluid channel 62 and the second fluid channel 64. The sensor 70' is located at least partially within the well 60 so that the temperature of the fluid flowing from the first fluid channel 62' to the second fluid channel 65' through the thermal well 60' is illustrated. The fluid flowing through the thermal well 60' may be controlled with an orifice 82. That is, should the amount of fluid traveling through the thermal well 60' between the first fluid channel 62' and the second fluid channel 64' be too great, the orifice 82 may restrict the flow therethrough. The orifice 82 may be controllable to vary during the operation of the rotating machine 10'. As is illustrated in FIG. 3, the first fluid channel 62' and the second fluid channel 64' are disposed relatively far apart. That is, the first fluid channel 62' is located close to the pump impeller 22 and the second fluid channel 64 is located close to the turbine impeller 24.

Figure 4:
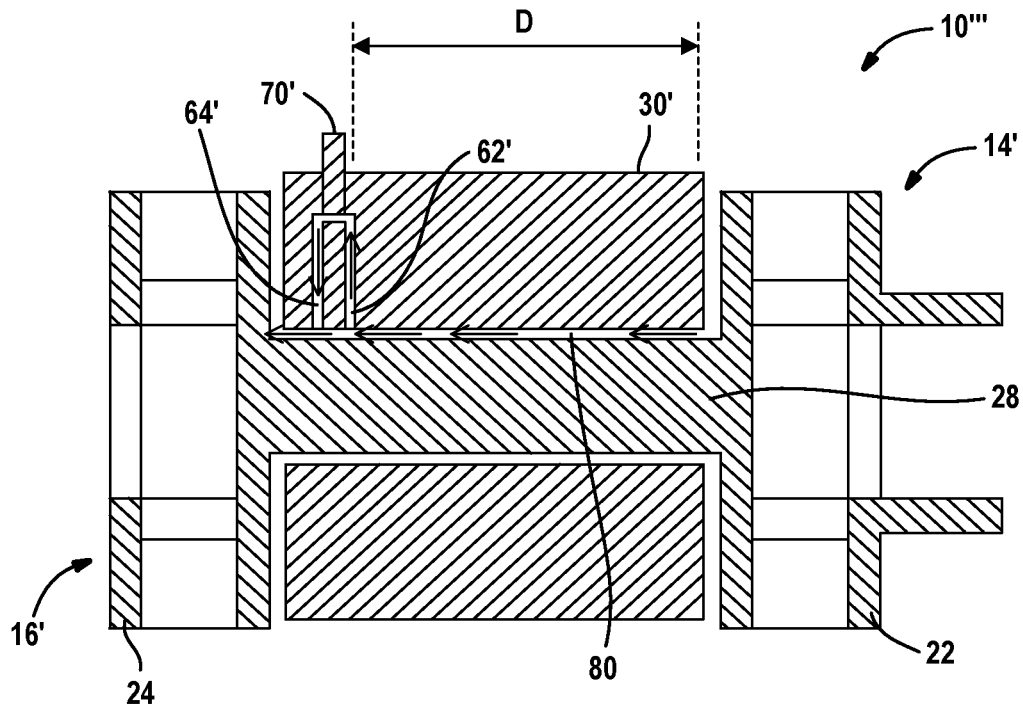
FIG. 4 is a cross-sectional view of a second example of a rotor shaft and journal bearing according to the present disclosure.

Referring now to FIG. 4, the location of the first fluid channel 62' is moved closer to the turbine impeller 24 in the rotary machine 10'''. This allows a greater distance of the journal bearing 30 to be monitored during operations. The location D of the first fluid channel 62' may be located as close to the second fluid channel 64' as will permit a sufficient differential pressure between the first fluid channel 62' and the second fluid channel 64' to induce the movement of fluid through the thermal wells 60'. The closer the first fluid channel 62' is to the second fluid channel 64', the greater the monitored distance of the journal bearing 30.

As mentioned above, the sensor 70 may be a temperature sensor, a particulate sensor or another type of sensor. A particulate sensor measures the debris or containments in the lubricant. Of course, a temperature sensor and particulate sensor may be used together within the thermal well 60. Another type of sensor may also monitor changes to the fluid to detect failure.

Figure 5:
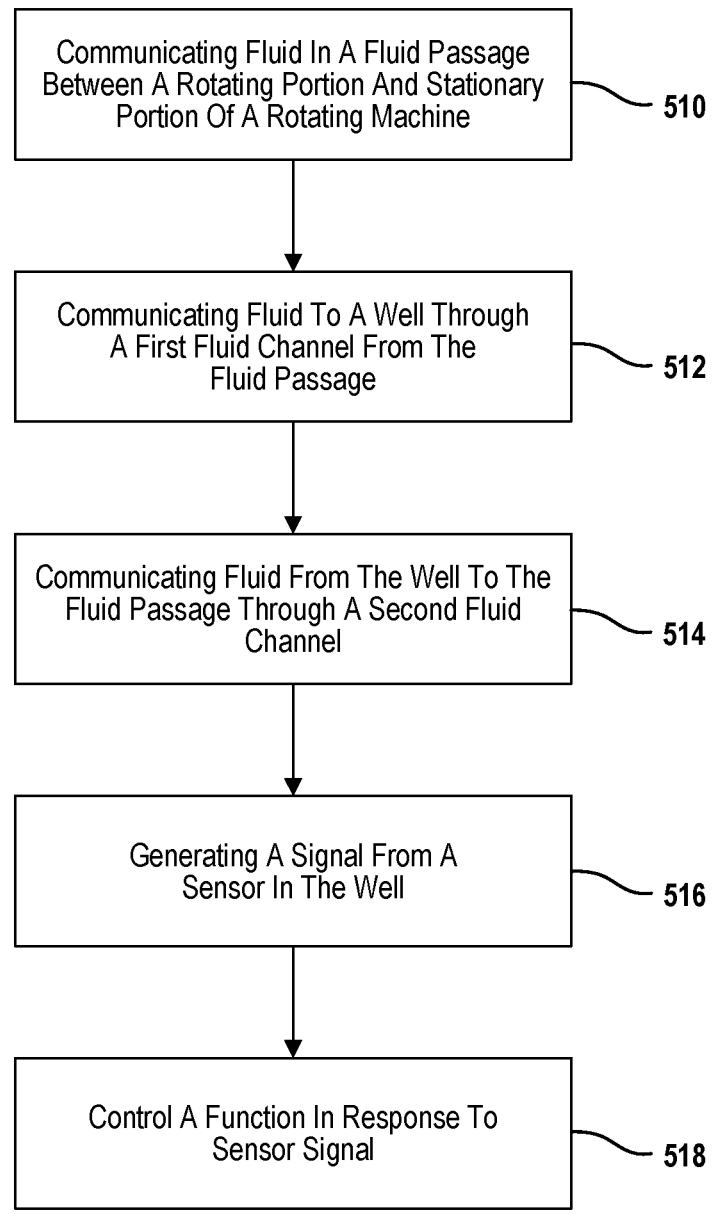
FIG. 5 is a flow chart of a method for operating a rotating machine.

Referring now to FIG. 5, a method of operating the rotating machine is set forth. In step 510, fluid is communicated in a fluid passage between a rotating portion and a stationary portion of a rotating machine. In step 512, fluid is communicated to a well through a first fluid channel. In step 514, fluid is communicated from the well to the fluid passage through a second fluid channel. In step 516, a sensor within the well generates a signal characteristic of a change of the fluid within the well such as temperature or particulates. In step 518, a function is controlled in response to the sensor signal. When the signal is a temperature signal, valves or other types of process control may be changed. As mentioned above, the sensor may be something other than a temperature signal. That is, a particulate sensor may be used to sense particles within the fluid. A valve or other process may be changed in response to sensing particles in the lubricating fluid.

Those skilled in the art can now appreciate from the foregoing description that the broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification and the following claims.

What is claimed is:

1. A rotating machine comprising:
   a stationary portion;
   a rotating portion, the stationary portion and the rotating portion having a fluid passage therebetween;
   said stationary portion comprising a first fluid channel, a well, and a second fluid channel spaced apart from the first fluid channel, the first fluid channel, the well and the second fluid channel formed within the stationary portion outside of the rotating portion, said first fluid channel fluidically communicating fluid from the fluid passage to the well, said second fluid channel fluidically communicating fluid from the well to the fluid passage; and
   a sensor coupled to the stationary portion and disposed at the well.

2. The rotating machine as recited in claim 1 wherein the first fluid channel comprises a first inlet coupled to the fluid passage and a first outlet coupled to the well, and the second fluid channel comprises a second inlet coupled to the well and a second outlet coupled to the fluid passage.

3. The rotating machine as recited in claim 2 wherein a first pressure at the first inlet of the first fluid channel is higher than a second pressure at the second outlet of the second fluid channel.

4. The rotating machine as recited in claim 1 wherein the rotating portion comprises an impeller disposed on a shaft having a longitudinal axis, and wherein the first fluid channel is disposed a first distance from the longitudinal axis and the second fluid channel is disposed a second distance from the longitudinal axis greater than the first distance.

5. The rotating machine as recited in claim 4 wherein the impeller comprises a turbine impeller.

6. The rotating machine as recited in claim 1 wherein the first fluid channel and the second fluid channel are coupled to a pocket fluidically coupled to the fluid passage.

7. The rotating machine as recited in claim 6 wherein the pocket is disposed between an inner land and an outer land of a thrust bearing.

8. The rotating machine as recited in claim 1 wherein the stationary portion comprises a journal bearing and the rotating portion comprises a shaft.

9. The rotating machine as recited in claim 1 wherein the stationary portion comprises a journal bearing and the rotating portion comprises a shaft disposed between a pump impeller and a turbine impeller.

10. The rotating machine as recited in claim 1 wherein the stationary portion comprises a thrust bearing and the rotating portion comprises a turbine impeller.

11. The rotating machine as recited in claim 1 wherein the sensor comprises a temperature sensor.

12. The rotating machine as recited in claim 1 wherein the sensor comprises a particulate sensor.

13. A turbocharger comprising:
    the rotating machine of claim 1;
    wherein the stationary portion comprises an inner land and an outer land; and
    wherein the rotating portion comprises a turbine impeller.

14. A system comprising:
    a turbocharger as recited in claim 13;
    a valve; and
    a controller receiving a temperature signal from the sensor controlling the valve in response to the temperature signal.

15. A turbocharger comprising:
    the rotating machine of claim 1;
    wherein the stationary portion comprises a journal bearing; and
    wherein the rotating portion comprises a shaft disposed between a turbine impeller and a pump impeller.

16. The turbocharger of claim 15 wherein the first fluid channel is located a first distance from the pump impeller and the second fluid channel is located a second distance from the pump impeller, said second distance greater than the first distance.

17. A method of determining a sensed condition for a rotating machine comprising:
    communicating a fluid through a fluid passage between a rotating portion and a stationary portion of the rotating machine;
    communicating the fluid from the fluid passage to a well through a first fluid channel;
    communicating fluid from the well to the fluid passage through a second fluid channel, the first fluid channel, the well and the second fluid channel formed within the stationary portion outside of the rotating portion; and
    generating a sensor signal at a sensor operably coupled to the well corresponding to the sensed condition.

18. The method of claim 17 further comprising communicating the sensor signal to a controller and controlling a function in response to the sensor signal.

19. The method of claim 18 wherein controlling a function comprises controlling a valve.

20. The method of claim 18 wherein generating the sensor signal comprises generating a temperature signal and wherein the controller controls the function based on the temperature signal.

* * * * *